(12) United States Patent
Tang et al.

(10) Patent No.: US 9,761,404 B2
(45) Date of Patent: *Sep. 12, 2017

(54) X-RAY APPARATUS AND A CT DEVICE HAVING THE SAME

(71) Applicants: TSINGHUA UNIVERSITY, Beijing (CN); NUCTECH COMPANY LIMITED, Beijing (CN)

(72) Inventors: Chuanxiang Tang, Beijing (CN); Huaping Tang, Beijing (CN); Huaibi Chen, Beijing (CN); Wenhui Huang, Beijing (CN); Huayi Zhang, Beijing (CN); Shuxin Zheng, Beijing (CN); Yaohong Liu, Beijing (CN); Jinsheng Liu, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 182 days.

This patent is subject to a terminal disclaimer.

(21) Appl. No.: 14/490,509

(22) Filed: Sep. 18, 2014

(65) Prior Publication Data
US 2015/0078511 A1    Mar. 19, 2015

(30) Foreign Application Priority Data
Sep. 18, 2013 (CN) .......................... 2013 1 0427203

(51) Int. Cl.
  *H01J 35/06* (2006.01)
  *H01J 35/04* (2006.01)
  *H01J 35/10* (2006.01)
  *H01J 35/14* (2006.01)
  *H01J 35/16* (2006.01)
  *G01N 23/04* (2006.01)

(52) U.S. Cl.
  CPC .......... *H01J 35/045* (2013.01); *G01N 23/046* (2013.01); *H01J 35/06* (2013.01);
(Continued)

(58) Field of Classification Search
CPC ....... A61B 6/032; A61B 6/035; A61B 6/4007; A61B 6/4014; A61B 6/4021;
(Continued)

(56) References Cited

U.S. PATENT DOCUMENTS

| 7,317,783 | B2 | 1/2008 | Dolgonos |
| 7,512,215 | B2* | 3/2009 | Morton ................... H01J 35/04 378/10 |
| 2003/0072407 | A1* | 4/2003 | Mihara ................... A61B 6/032 378/4 |

(Continued)

FOREIGN PATENT DOCUMENTS

| CN | 102592927 A | 7/2012 |
| CN | 202502979 U | 10/2012 |
| CN | 102842477 A | 12/2012 |
| CN | 102988076 A | 3/2013 |
| CN | 103077874 A | 5/2013 |
| CN | 103219212 A | 7/2013 |
| CN | 203192747 U | 9/2013 |
| CN | 203537653 U | 4/2014 |

(Continued)

*Primary Examiner* — Jurie Yun
(74) *Attorney, Agent, or Firm* — McDermott Will & Emery LLP (57) ABSTRACT

A x-ray apparatus of the present application comprises: a vacuum box which is sealed at its periphery, and the interior thereof is high vacuum; a plurality of electron transmitting units arranged in a linear array and installed on the wall at one end within the vacuum box, each electron transmitting unit is independent to each other; the electron transmitting unit having: a heating filament; a cathode connected to the heating filament; a grid arranged above the cathode opposing the cathode; anode made of metal and installed at the other end of the vacuum box, and in the direction of length, the anode is parallel to the plane of the grid of the electron transmitting unit, and in the direction of width, the anode has a predetermined angle with respect to the plane of the grid of the electron transmitting unit.

18 Claims, 6 Drawing Sheets

(52) U.S. Cl.
CPC ............ *H01J 35/065* (2013.01); *H01J 35/10* (2013.01); *H01J 35/14* (2013.01); *H01J 35/16* (2013.01); *H01J 2235/087* (2013.01)

(58) Field of Classification Search
CPC ........ A61B 6/4028; H01J 35/02; H01J 35/04; H01J 35/045; H01J 35/06; H01J 35/065; H01J 35/08; H01J 35/14; H01J 35/16; H01J 2235/06; H01J 2235/062; H01J 2235/068; H01J 2235/086; H05G 1/52
USPC ......... 378/4, 9, 10, 122, 123, 124, 134, 136, 378/137, 138
See application file for complete search history.

(56) References Cited

U.S. PATENT DOCUMENTS

2007/0248213 A1    10/2007    Dolgonos

FOREIGN PATENT DOCUMENTS

| CN | 203563254 U | 4/2014 |
|----|-------------|--------|
| CN | 203590580 U | 5/2014 |
| CN | 203734907 U | 7/2014 |
| CN | 104470178 A | 3/2015 |
| EP | 1277439 A1 | 1/2003 |
| WO | WO-2015/039602 A1 | 3/2015 |

* cited by examiner

X-RAY APPARATUS AND A CT DEVICE HAVING THE SAME

TECHNICAL FIELD

The present application relates to an apparatus generating distributed x-ray, in particular to a grid-controlled distributed x-ray apparatus generating x-ray altering the position of focus in a predetermined order by arranging a plurality of independent electron transmitting units and controlling the electron transmitting unit by the grid in a x-ray light source device and a CT device having the grid-controlled distributed x-ray apparatus.

BACKGROUND

In general, x-ray light source refers to a device generating x-ray which is usually composed of x-ray tube, power supply and control system, auxiliary apparatus for cooling and shielding etc. or the like. The core of the device is the x-ray tube. The X-ray tube usually consists of cathode, anode, glass or ceramic housing etc. The cathode is a directly-heated spiral tungsten filament. When in operation, it is heated to a high-temperature state by current, thus generating thermal-transmitted electronic beam current. The cathode is surrounded by a metal cover having a slit in the front end thereof and focusing the electrons. The anode is a tungsten target inlayed in the end surface of the copper billet. When in operation, a high pressure is applied between the cathode and anode. The electrons generated by the cathode move towards the anode under the effect of electric field and ram the surface of the target, thereby the x-ray is generated.

X-ray presents a wide range of applications in the fields of nondestructive detection, security check and medical diagnoses and treatment etc. In particular, the x-ray fluoroscopic imaging device utilizing the high penetrability of the x-ray plays a vital role in every aspect of people's daily lives. The early device of this type is a film flat fluoroscopic imaging device. Currently, the advanced technology is digital, multiple visual angles and high resolution stereoscopic imaging device, e.g. CT (computed tomography), being able to obtain three-dimensional graphs or slice image of high definition, which is an advanced application.

In the current CT device, the x-ray source and the detector need to move on the slip ring. In order to increase the speed of inspection, the moving speeds of x-ray source and the detector are normally high leading to a decreased overall reliability and stabilization. In addition, due to the limit of moving speed, the inspection speed of the CT is limited accordingly. Therefore, there is a need for the x-ray source generating multiple visual angles without displacing.

To address the problems of reliability, stabilization and inspection speed caused by the slip ring as well as the heat resistance problem of the anode target spot, there are methods provided in the available patent literature. For example, a rotating target x-ray source can solve the overheat of the anode target to some extent. However, its structure is complex and the target spot generating x-ray is still a definite target spot position with respect to the overall x-ray source. For instance, in some technology, a plurality of dependent conventional x-ray sources are arranged closely in a periphery to replace the movement of x-ray source in order to realize multiple visual angles of a fixed x-ray source. Although multiple visual angles can be realized, the cost is high. In addition, the space between the target spots of different visual angles is big and the imaging quality (stereoscopic resolution) is quite poor. What's more, a light source generating distributed x-ray and the method thereof is disclosed in the patent literature 1 (U.S. Pat. No. 4,926,452), wherein the anode target has a large area remitting the overheat of the target and multiple visual angles could be produced since the position of target spot changes along the periphery. Although the patent literature 1 performs scanning deflection to the accelerated high-energy electron beam, there are still problems of difficult control, non-disjunction of target spots and poor repeatability. Anyway, it is still an effective way to generate distributed light sources. Moreover, the light sources generating distributed x-ray and methods thereof are proposed in the patent literature 2 (US20110075802) and patent literature 3 (WO2011/119629), wherein the anode target has a large area remitting the overheat of the target and multiple visual angles could be produced since the position of target spots are fixed dispersedly and are arranged in an array. In addition, CNTs (carbon nano tubes) are employed as cold cathodes and the cold cathodes are arranged in an array. The transmitting is controlled by utilizing the voltage between cathode and grid so as to control each cathode to emit electron in sequence and bombard the target spot on the anode in an order correspondingly, thus becoming the distributed x-ray source. However, there are disadvantages of complex manufacturing process and poor transmitting capability and short lifetime of carbon nano tubes.

SUMMARY

The present application is proposed to address the above-mentioned problem. It aims at providing a grid-controlled distributed x-ray apparatus and a CT device having the same such that multiple visual angles can be generated without moving the light source which contributes to simplify the structure, enhance the stability and reliability of the system, hence increasing the efficiency of inspection.

To achieve the above purposes, the disclosure provides a grid-controlled distributed x-ray apparatus comprises: a vacuum box which is sealed at its periphery, and the interior thereof is high vacuum; a plurality of electron transmitting units arranged in a linear array and installed on the wall at one end within the vacuum box, each electron transmitting unit is independent to each other; anode installed at the other end within the vacuum box, and in the direction of length, the anode is parallel to the plane of the grid of the electron transmitting unit, and in the direction of width, the anode has a predetermined angle with respect to the plane of the grid of the electron transmitting unit; power supply and control system having a high voltage power supply connected to the anode, a filament power supply connected to each of the plurality of the electron transmitting units, a grid-controlled apparatus connected to each of the plurality of electron transmitting units, a control system for controlling each power supply; the electron transmitting unit having: a heating filament; a cathode connected to the heating filament; a filament lead extending from both ends of the heating filament and connected to the filament power supply; a grid arranged above the cathode opposing the cathode; an insulated support having opening and enclosing the heating filament and the cathode; a connecting fastener connected at the periphery of the lower end of the insulated support and sealed connected to the wall of the vacuum box; the grid having: a grid frame which is made of metal and provided with opening in the center; a grid mesh which is made of metal and fixed at the position of the opening of the grid frame; a grid lead, extending from the grid frame and connected to the grid-controlled apparatus. The grid is configured on the opening of the insulated support opposing the cathode. The filament lead and the grid lead pass through the insulated support extending to the outside from the electron transmitting unit.

In addition, in the grid-controlled distributed x-ray apparatus according to the present application, it further comprises: a high voltage power supply connecting means connecting the anode to the cable of the high voltage power supply and installed on the side wall of the vacuum box at the end adjacent to the anode, a filament power supply connecting means for connecting the heating filament to the filament power supply, and a connecting means of grid-controlled apparatus for connecting the grid of the electron transmitting unit to the grid-controlled apparatus.

In addition, in the grid-controlled distributed x-ray apparatus according to the present application, the center of the opening of the grid is aligned with the center of the cathode and the shape of the opening is corresponding to that of the cathode.

In addition, in the grid-controlled distributed x-ray apparatus according to the present application, the insulated support is cylinder, and the grid frame, the cathode and the grid mesh are circular.

In addition, in the grid-controlled distributed x-ray apparatus according to the present application, the insulated support is cylinder, and the grid frame, the cathode and the grid mesh are rectangular.

In addition, in the grid-controlled distributed x-ray apparatus according to the present application, the insulated support is cuboid, and the grid frame, the cathode and the grid mesh are circular.

In addition, in the grid-controlled distributed x-ray apparatus according to the present application, the insulated support is cuboid, and the grid frame, the cathode and the grid mesh are rectangular.

In addition, in the grid-controlled distributed x-ray apparatus according to the present application, the grid mesh is flat, spherical or U-shaped groove.

In addition, in the grid-controlled distributed x-ray apparatus according to the present application, the vacuum box is made of glass or ceramic.

In addition, in the grid-controlled distributed x-ray apparatus according to the present application, the vacuum box is made of metal.

In addition, in the grid-controlled distributed x-ray apparatus according to the present application, it further comprises: a vacuum power supply included in the power supply and control system; a vacuum means installed on the side wall of the vacuum box maintaining the high vacuum in the vacuum box by using the vacuum power supply.

In addition, in the grid-controlled distributed x-ray apparatus according to the present application, the plurality of electron transmitting units are linear or segmented linear.

In addition, in the grid-controlled distributed x-ray apparatus according to the present application, the plurality of electron transmitting units are arc or segmented arc.

In addition, in the grid-controlled distributed x-ray apparatus according to the present application, the arrangement space between each electron transmitting unit is uniform.

In addition, in the grid-controlled distributed x-ray apparatus according to the present application, the arrangement space between each electron transmitting unit is nonuniform.

In addition, in the grid-controlled distributed x-ray apparatus according to the present application, the grid-controlled apparatus comprises a controller, a negative high voltage module, a positive high voltage module, and a plurality of high voltage switch elements, each of the plurality of high voltage switch elements at least comprises a control end, two input ends, an output end, a withstand voltage between each end must be larger than the maximum voltage formed by the negative high voltage module and the positive high voltage module, the negative high voltage module provides a stable negative high voltage to one input end of each of the plurality of high voltage switch elements, the positive high voltage module provides a stable positive high voltage to the other input end of each of the plurality of high voltage switch elements, the controller controls independently each of the plurality of high voltage switch elements, the grid-controlled apparatus further comprises a plurality of control signal output channel, one output end of the high voltage switch element is connected to one of the control signal output channel.

In addition, the present application also provides a CT device, wherein the x-ray resource used is the grid-controlled distributed x-ray apparatus as mentioned above.

According to the present application, provided is a grid-controlled distributed x-ray apparatus generating x-ray altering the position of focus in a certain order in a light source device. By employing the thermionic cathode, the electron transmitting unit of this disclosure has the advantages of larger transmitting current, longer service life and more matured technology compared with other current design. It is easy to assemble, flexible to control and convenient to maintain because multiple electron transmitting units are fixed to the vacuum box respectively. The state conversion can be prompt and concise and it is ready to make out multiple operating states by controlling the operating state of each electron transmitting unit via the control of the grid. The overheat of the anode is remitted by employing the design of big anode in the shape of strip thus improving the power of the light source. The electron transmitting units can be in a linear arrangement rendering the overall to be a linear distributed x-ray apparatus or an annular arrangement rendering the overall to be an annular distributed x-ray apparatus, so as to meet various service conditions and have flexible applications. By the design to control the voltage via grid, an automatic focusing effect of the electron beam generated by each electron transmitting unit can be obtained and small target spot could be achieved. Compared with other distributed x-ray light source device, the one in this disclosure has the advantages of large current, small target spot, uniform target spots and high repeatability, high output power, simple structure, convenient control and low cost.

Applying the grid-controlled distributed x-ray light source to the CT device, multiple visual angles can be generated without moving the light source, and therefore the movement of slip ring could be omitted. This contributes to simplify the structure, enhance the stability and reliability of the system, hence increasing the efficiency of inspection.

DETAILED DESCRIPTION OF THE PREFERRED EMBODIMENTS

Hereinafter, detailed description of the present disclosure will be given in combination with the accompanying drawings.

Figure 1:
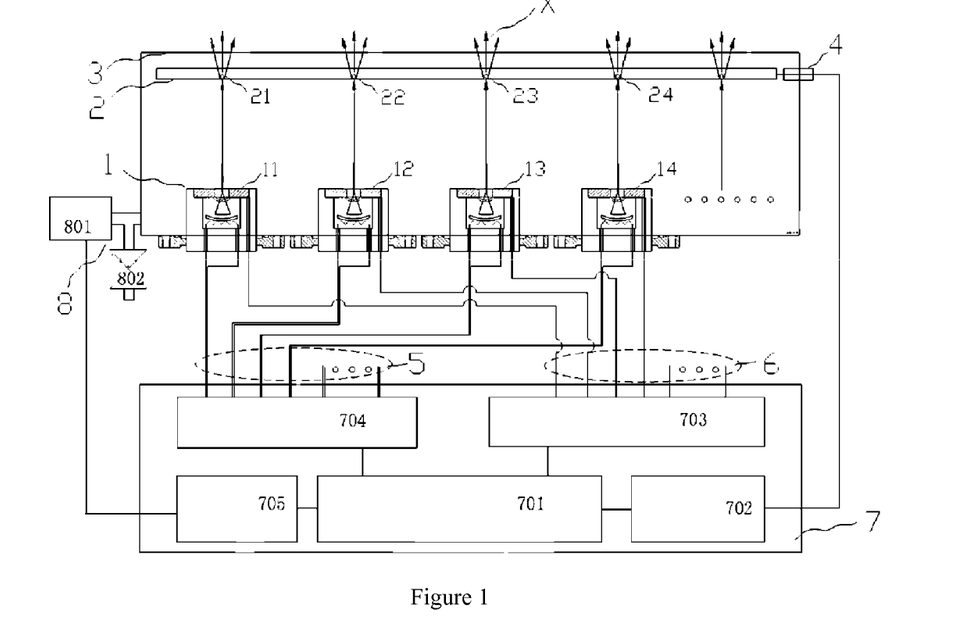
FIG. 1 depicts a schematic view of the structure of the grid-controlled distributed x-ray apparatus of the present application.
Figure 2:
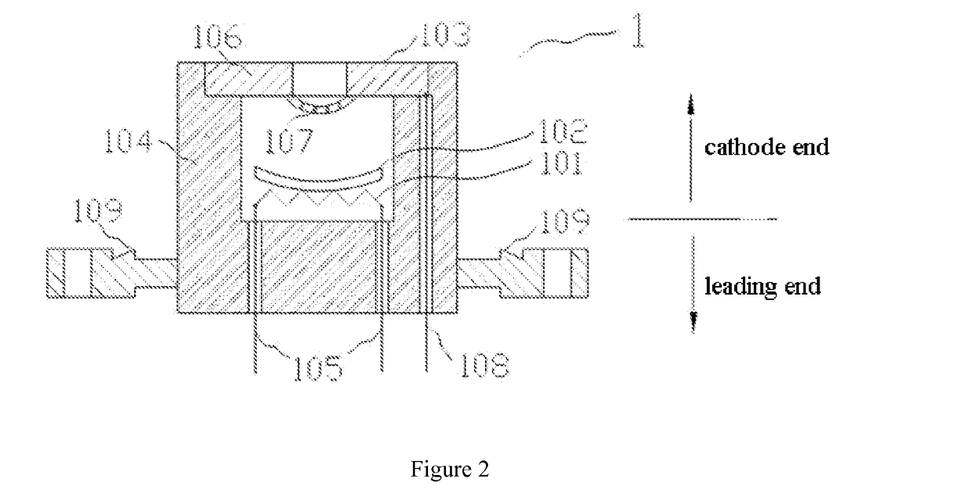
FIG. 2 depicts a schematic view of the structure of an electron transmitting unit in the present application.

FIG. 1 is a schematic view of the structure of the grid-controlled distributed x-ray apparatus of the present application. FIG. 2 is a schematic view of the structure of an electron transmitting unit in the present application. As shown in FIG. 1, the grid-controlled distributed x-ray apparatus of the present application includes a plurality of electron transmitting units 1 (at least two, hereinafter also specifically referred to as electron transmitting unit 11, 12, 13, 14), an anode 2, a vacuum box 3, a high voltage power supply connecting means 4, a filament power supply connecting means 5, a connecting means of grid-controlled apparatus 6 and a power supply and control system 7. In addition, the electron transmitting unit 1 includes a heating filament 101, a cathode 102, a grid 103, an insulated support 104, a connecting fastener 109 etc. The plurality of electron transmitting units 1 are arranged in a straight line and the anode 2 is in a shape of strip that corresponds to the arrangement of the electron transmitting units 1. In addition, anode 2 is parallel to the straight line arranged by the plurality of electron transmitting units 1. The high voltage power supply connecting means 4 is installed on the wall of the vacuum box 3 and constitutes an overall seal structure together with the vacuum box 3.

The electron transmitting units 1 are used to generate electron beam current as required and are installed on the walls at an end of the vacuum box 3 (herein defined as the bottom end, c.f. FIG. 1) constituting an overall seal structure together with the wall of the vacuum box 3 by the connecting fastener 109. However, the embodiments are not limited thereto. Other installing ways could be adopted as long as the electron transmitting units 1 can be installed in the vacuum box 3. Moreover, the cathode end (including a heating filament 101, a cathode 102, a grid 103) of the electron transmitting unit 1 is located inside the vacuum box and the lead end (including a filament lead 105, a grid lead 108, a connecting fastener 109) of the electron transmitting unit 1 extends to the outside of the vacuum box. But the embodiments are not limited thereto. Other ways may be adopted. Additionally, a structure of electron transmitting unit 1 is shown in FIG. 2. The electron transmitting unit 1 includes a heating filament 101, a cathode 102, a grid 103, an insulated support 104, a filament lead 105, a connecting fastener 109 and the grid 103 is consist of a grid frame 106, a grid mesh 107, a grid lead 108. The cathode 102 is connected to the heating filament 101 which is usually made of tungsten filament. Cathode 102 is made of materials of strong capability to thermal transmit electron, such as baryta, scandate, lanthanum hexaborides etc. The insulated support 104 surrounding the heating filament 101 and the cathode 102 is equivalent to the housing of electron transmitting unit 1 and are made of insulated material, in most cases ceramic. The filament lead 105 extends to the lower end of the electron transmitting unit 1 through the insulated support 104 (the embodiment is not limited thereto as long as the filament lead 105 can extend to the outside of the electron transmitting unit 1). Between the filament lead 105 and the insulated support 104 is a seal structure. Grid 103 is located at the upper end of the insulated support 104 (namely, it is located at the opening of the insulated support 104) opposing the cathode 102, preferably grid 103 is aligned with the center of the cathode 102 vertically. Moreover, the grid 103 includes a grid frame 106, a grid mesh 107, a grid lead 108, all of which are made of metal. Normally, the grid frame is made of stainless steel material, grid mesh 107 molybdenum material, and grid lead 108 Kovar (alloy) material. The grid lead 108 extends to the lower end of the electron transmitting unit 1 through the insulated support 104 (the embodiment is not limited thereto as long as the grid lead 108 can extend to the outside of the electron transmitting unit 1). Between the grid lead 108 and the insulated support 104 is a seal structure.

What's more, in particular, with respect to the structure of the grid 103, the main body thereof is a piece of metal plate (e.g. stainless steel material), that is the grid frame 106. An opening is provided at the center of the grid frame 106, the shape thereof can be square or circular etc. A wire mesh (e.g. molybdenum material) is fixed at the position of opening, namely the grid mesh 107. Moreover, a lead (e.g. Kovar alloy material), namely the grid lead 108, extends from somewhere of the metal plate such that the grid 103 can be connected to an electric potential. Additionally, the grid 103 is positioned right above the cathode 102. The center of the above-mentioned opening of the grid 103 sis aligned with the center of the cathode 102 (namely in a vertical line longitudinally). The shape of the opening is corresponding to that of the cathode 102. In usual, the opening is smaller than the area of cathode 102. However, the structure of the grid 103 is not limited to those described above as long as the electron beam current is able to pass the grid 103. In addition, the grid 103 is fixed with respect to cathode 102 by the insulated support 104.

What's more, in particular, with respect to the structure of the connecting fastener 109, preferably, the main body thereof is a circular knife edge flange with opening provided in the center. The shape of the opening may be square or circular etc. Seal connection can be provided at the opening and the outer edge of the lower end of the insulated support 104, for example, welding connection. Screw holes are formed at the outer edge of the knife edge flange. The electron transmitting unit 1 can be fixed to the walls of the vacuum box 3 by bolted connection. A vacuum seal connection is formed between the knife edge and the wall of the vacuum box 3. This is a flexible structure easy for disassemble where certain one of multiple electron transmitting units 1 breaks down it can be replaced easily. It should be noted that the connecting fastener 109 functions to achieve the seal connection between the insulated support 104 and the vacuum box 3 and various ways may be employed, for example, transition welding by metal flange, or glass high temperature melting seal connection, or welding to the metal after ceramic metallizing etc.

Figure 3:
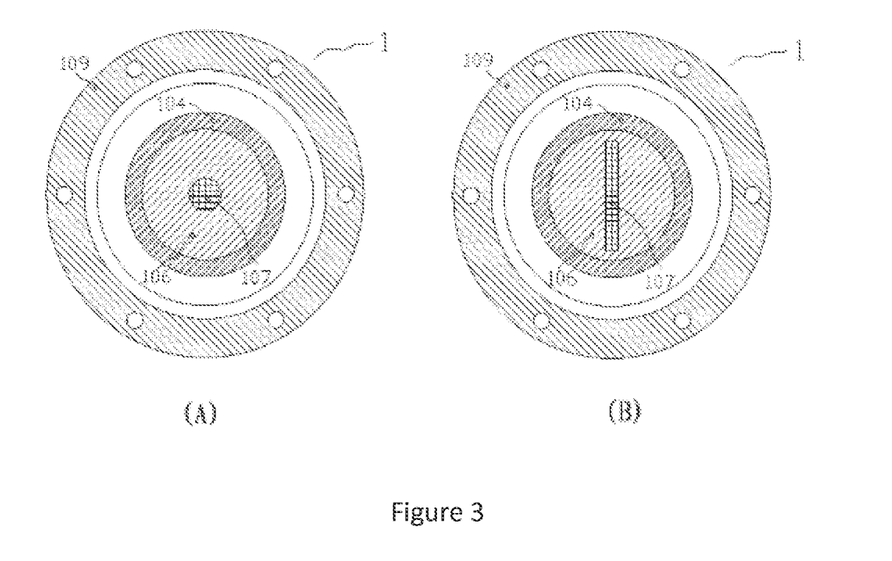
FIG. 3 depicts the top view of the structure of a cylinder electron transmitting unit in the present application, wherein (A) is the case of circular grid hole and (B) is the case of rectangular grid hole.
Figure 5:
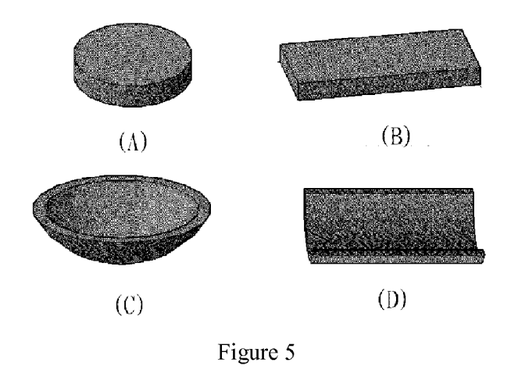
FIG. 5 depicts a schematic view of the structure of a cathode, wherein (A) is a flat circular cathode, (B) is a flat rectangular cathode, (C) is a spherical arc cathode, and (D) is a cylindrical surface cathode.

In addition, electron transmitting unit 1 may be a structure of cylinder, that is, the insulated support 104 is cylinder, while cathode 102, grid frame 106, grid mesh 107 can be circular simultaneously or be rectangular simultaneously. FIG. 3 is the top view of the structure of a cylinder electron transmitting unit 1 in the present application, wherein (A) depicts the structure where cathode 102, grid frame 106, and grid mesh 107 are circular simultaneously and (B) depicts the structure where cathode 102, grid frame 106 and grid mesh 107 are rectangular simultaneously. In addition, as to the circular cathode, in order to achieve better focusing effect of the electron generated by the surface of cathode 102, it typically machines the surface of cathode 102 into spherical arc shape (as shown in FIG. 5 (C)). The diameter of the surface of cathode 102 is typically several mm, for example 2 mm in diameter. The diameter of the opening of the grid mesh 107 installed on the grid frame 106 is typically several mm, for example 1 mm in diameter. In addition, the distance from the grid 103 to the surface of the cathode 102 is typically a few tenths of an mm to a few mms, e.g. 2 mm. Moreover, as to rectangular cathode, in order to achieve better focusing effect of the electron generated by the surface of cathode 102, it typically employs the cylindrical surface to facilitate further converging the electron beam current on the narrow side. Typically, the length of the arc surface ranges from several mm to dozens of mms, and the width is usually several mm, e.g. 10 mm in length and 2 mm in width. Correspondingly, the grid mesh 107 is rectangular, preferably the width thereof is 1 mm and the length thereof is 10 mm. In FIG. 5, four cases are shown in which the cathodes 102 are flat circular, flat rectangular, spherical arc and cylinder arc surface respectively.

Figure 4:
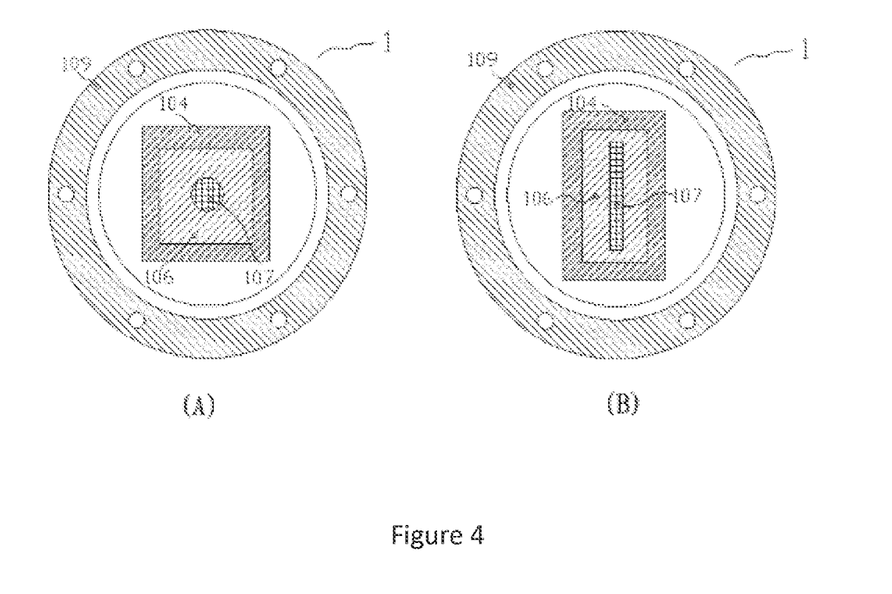
FIG. 4 depicts the top view of the structure of a cuboid electron transmitting unit in the present application, wherein (A) is the case of circular grid hole and (B) is the case of rectangular grid hole.

In addition, the electron transmitting unit 1 may be cuboid structure, namely the insulated support 104 is cuboid, while the cathode 102, the grid frame 106, the grid mesh 107 may be circular simultaneously or rectangular simultaneously. FIG. 4 is the top view of the structure of a cuboid electron transmitting unit 1, wherein (A) depicts the structure where cathode 102, grid frame 106, and grid mesh 107 are circular simultaneously and (B) depicts the structure where cathode 102, grid frame 106 and grid mesh 107 are rectangular simultaneously. It should be noted that twill lines in FIGS. 3 and 4 are depicted for the purpose of distinguishing various different components, not representing a cross section.

Figure 6:
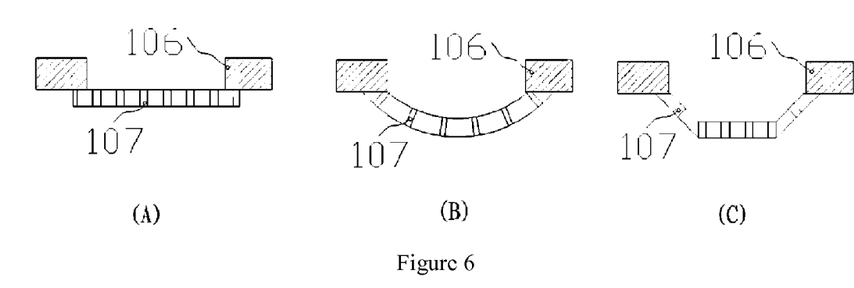
FIG. 6 depicts a schematic view of the structure of the grid mesh in the present application, wherein (A) is a flat grid mesh, (B) is a spherical grid mesh, and (C) is U-shaped groove grid mesh.

What's more, in particular, with respect to the structure of the grid mesh 107, as shown in FIG. 6, it can be flat, or spherical or U-shaped groove shape as well. Spherical type is preferable because spherical grid mesh can produce better focusing effect of the electron beam.

Figure 7:
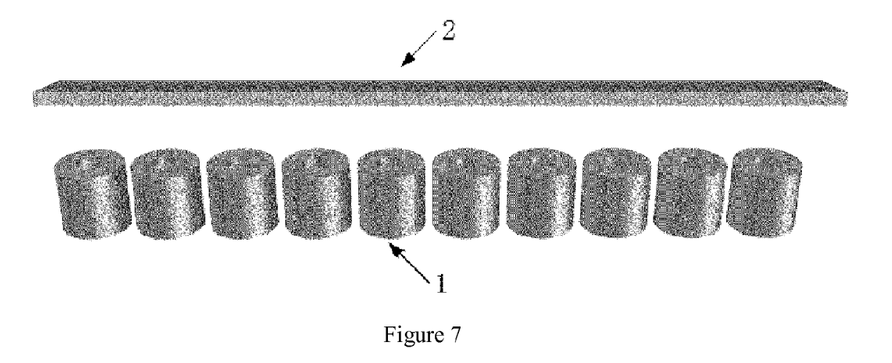
FIG. 7 depicts a schematic front view of the configuration of electron transmitting unit and the anode inside the distributed x-ray apparatus in line arrangement according to the present application.
Figure 8:
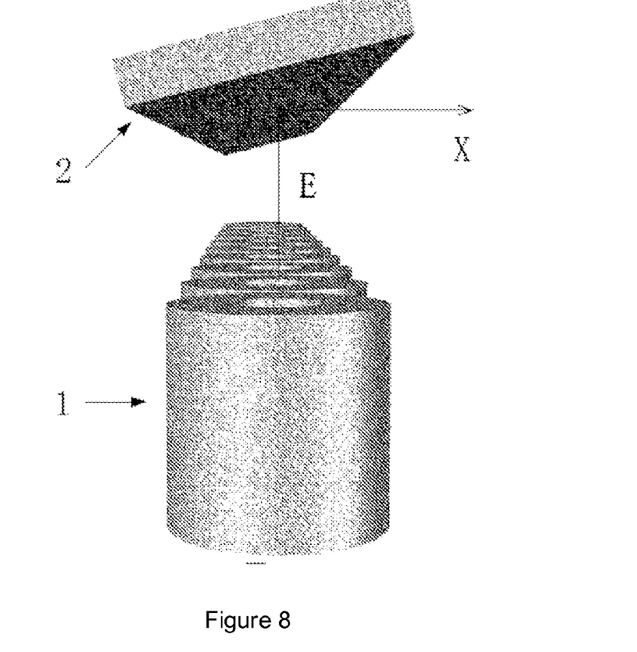
FIG. 8 depicts a schematic side view of the configuration of electron transmitting unit and the anode inside the distributed x-ray apparatus in line arrangement according to the present application.

In addition, the anode 2 is a metal in a shape of strip installing at the other end inside the vacuum box 3 (herein defined as the upper end, c.f. FIG. 1). Also, as shown in FIG. 7, along the direction of the length (left-right direction in FIGS. 1 and 7), it is parallel to the line along which the electron transmitting units 1 are arranged. Additionally, along the direction of width, the surface of the anode 2 has a small angle with respect to the plane of the surface of the electron transmitting unit 1. Typically, the angle ranges from several degrees to dozens of degrees (as shown in FIG. 8), typically 15 degrees. Normally, positive high voltage is applied on the anode 2, normally ranging from dozens of kv to hundreds of kv, typically e.g. 180 kv. Hence, the parallel high-voltage electric fields are formed between the anode 2 and the electron transmitting unit 1. The electron beam currents that pass through the grid mesh 107 are accelerated by the effect of the high-voltage electric field, moving opposing the direction of electric field and finally bombarding the anode 2, thus generating x-ray. Also, the anode 2 is preferably made of heat resisting materials, such as metal tungsten or tungsten alloy etc. It should be noted that the electron transmitting units 1 in FIGS. 7 and 8 only reflect the portions in the vacuum box 3 and the shape of the electron transmitting unit is cylinder.

In addition, the power supply and control system 7 includes a control system 701, a high voltage power supply 702, a grid-controlled apparatus 703, a filament power supply 704 etc. The High voltage power supply 702 is connected to the anode 2 by the high voltage power supply connecting means 4 installed on the wall of the vacuum box 3. The grid-controlled apparatus 703 is connected to each grid lead 108 respectively by the connecting means of grid-controlled apparatus 6. Normally, the number of electron transmitting units 1 is same as that of independent grid leads 108, and the number of the output lines of the grid-controlled apparatus 703 is same as that of the number of grid leads 108. The connection means of grid-controlled apparatus 6 is usually the cable with connector, the number of which is same as that of grid leads 108. Coaxial line with withstand voltage no less than 3 kv is preferred. The filament power supply 704 is connected to each filament lead 105 by the filament power supply connecting means 5. The filament power supply connecting means 5 is usually the cable with connector. Multiple two-core cables are preferred, the number of which is same as that of electron transmitting units 1. Preferably, the number of output loop of the filament power supply 704 is same as the number of electron transmitting units 1, hence one-to-one correspondence can be achieved and filament power of each electron transmitting unit 1 can be adjusted and controlled independently. In addition, the operating condition of the high voltage power supply 702, the grid-controlled apparatus 703, the filament power supply 704 etc may be controlled by the control system 701.

Figure 9:
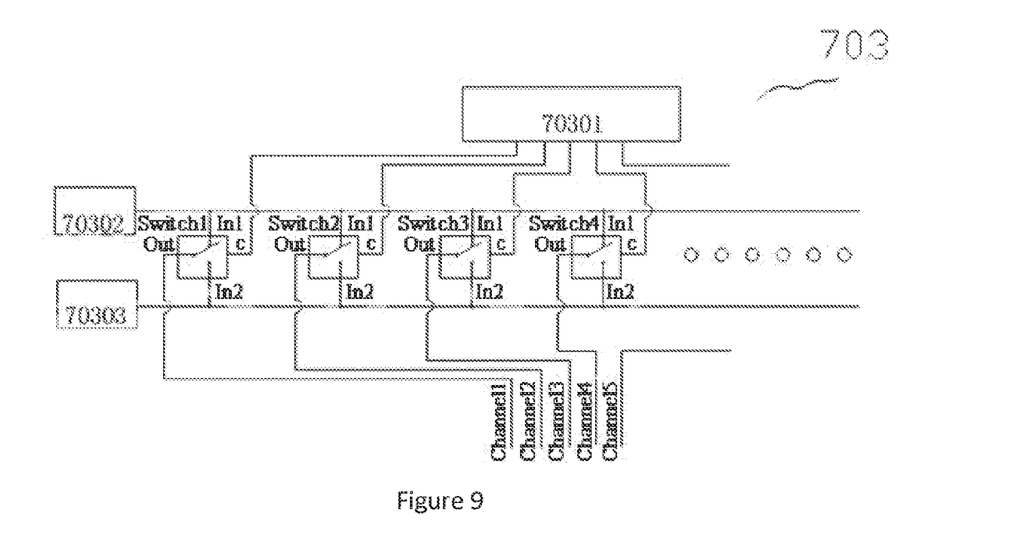
FIG. 9 depicts a schematic view of the structure of grid-controlled apparatus of the present application.

In addition, as shown in FIG. 9, the grid-controlled apparatus 703 includes a controller 70301, a negative high voltage module 70302, a positive high voltage module 70303 and a plurality of high voltage switch elements switch 1, switch 2, switch 3, and switch 4 . . . . Each of the plurality of high voltage switch elements at least includes a control end (C), two input ends (In1 and In2), an output end (Out). The withstand voltage between each end must be larger than the maximum voltage formed by the negative high voltage module 70302 and the positive high voltage module 70303 (that is to say, if the output of negative high voltage is −500V and the output of the positive high voltage is +2000V, the withstand voltage between each end must be larger than 2500V). The controller 70301 has multipath output, and each path is connected to the control end of a high voltage switch element. The negative high voltage module 70302 provides a stable negative high voltage, typically negative hundreds of volts. The range of negative high voltage can be 0V to −10 kV, and −500V is preferred. The negative high voltage is connected to one input end of each high voltage switch element. In addition, the positive high voltage module 70303 provides a stable positive high voltage, typically positive thousands of volts. The range of positive high voltage can be 0V to +10 kV, and +2000V is preferred. The positive high voltage is connected to the other input end of each high voltage switch element. The output end of each high voltage switch element is connected to control signal output channel channel1, channel 2, channel 3, channel 4, thus forming multipath to output control signal. Controller 70301 controls the operating state of each high voltage switch element such that the control signal of each output channel is negative high voltage or positive high voltage.

In addition, the power supply and control system 7 can adjust the current magnitude of each output loop of filament power supply 704 under different using condition so as to adjust the heating temperature that each heating filament 101 applies to the cathode 102 for changing the magnitude of transmitting current of each electron transmitting unit 1 and finally adjusting the intensity of x-ray transmitted each time. In addition, the intensity of the positive high voltage control signal for each output channel of the grid-controlled apparatus 703 can be adjusted so as to changing the magnitude of transmitting current of each electron transmitting unit 1 and finally adjusting the intensity of x-ray transmitted each time. Additional, the operating timing sequence and combining operating mode of each electron transmitting unit 1 can be programmed to realize flexible control.

In addition, the vacuum box 3 is a housing of a cavity with its periphery sealed. The interior is high vacuum and the housing is made of insulated materials such as glass or ceramic etc. Multiple electron transmitting units 1 arranged in a straight line are installed at the lower end (c.f. FIG. 1) of the vacuum box 3 and anode 2 in the shape of strip is installed at the upper end (c.f. FIG. 1). The anode 2 is parallel to the electron transmitting unit 1 in the direction of length. The space inside the vacuum box 3 is sufficient for the movement of electron beam current in the electric field without any obstruct. The high vacuum inside the vacuum 3 is obtained by baking and venting in the high temperature venting furnace with the vacuum degree better than $10^{-3}$ Pa, and the vacuum degree better than $10^{-5}$ Pa is preferred.

In addition, it is preferable that the housing of the vacuum box 3 is made of metal material. In such cases, the electron transmitting unit 1 is seal connected to the wall of the vacuum box 3 at the knife edge flange by its connecting fastener 109 and the anode 2 is fixed installed in the vacuum box 3 using the insulated supporting material. Also, the housing of the vacuum box 3 keeps sufficient distance from the electron transmitting unit 1 and anode 2 such that high voltage sparks will not occur and no substantial effect will be made to the electric field between the electron transmitting unit 1 and the anode 2.

In addition, the high voltage power supply connecting means 4 suitable for the cable connecting the anode 2 to the high voltage power supply 702 is installed on the side wall of vacuum box 3 adjacent to the anode 2. Normally, the high voltage power supply connecting mean 4 is a taper ceramic structure having metal column inside with one end connected to the anode 2 and the other end tightly connected to the wall of vacuum box 3, the whole of which forms a vacuum seal structure. The metal column 4 inside the high voltage power supply connecting means 4 is used such that the anode 2 is electrically connected to the cable joint of the high voltage power supply 702. Normally, the high voltage power supply connecting means 4 is designed to be pluggable to the cable joint.

In addition, the grid-controlled distributed x-ray apparatus of the present application may further include a vacuum means 8 including a vacuum pump 801 and a vacuum valve 802. The vacuum apparatus 8 is installed on the side wall of the vacuum box 3. The vacuum pump 801 works under the effect of the vacuum power supply 705 for maintaining the high vacuum in the vacuum box 3. Usually, when the grid-controlled distributed x-ray is operating, the electron beam current bombards the anode 2 which will emit heat and vent a small amount of gas. The gas may be withdrawn rapidly by using the vacuum pump 801 so as to maintain the high vacuum degree inside the vacuum box 3. A vacuum ion pump is preferably used as the vacuum pump 801. All metal vacuum valve which could withstand high temperature baking, e.g. all metal manual gate valve, is typically selected as the vacuum valve 802. Normally, the vacuum valve 802 is in the state of close. Correspondingly, the power supply and control system 7 of the grid-controlled distributed x-ray apparatus further includes the vacuum power supply 705 (Vacc PS) of the vacuum means 8.

It should be noted that the grid-controlled distributed x-ray apparatus of this disclosure is operated in the state of high vacuum. The method for obtaining and maintaining the high vacuum includes: completing installing the anode 2 in the vacuum box 3; completing seal connecting the high voltage power supply connecting means 4 and the vacuum mean 8 to the wall of vacuum box 3; sealing with a blind flange at the lower end of the vacuum box 3 to which the electron transmitting unit is connected firstly so as to form an integral seal structure of the vacuum box 3; then baking the structure in a vacuum furnace to vent gas and connecting the vacuum valve 82 to an external vacuum sucking system so as to vent the gas absorbed by the material of each component; then, in a normal temperature and clean environment, injecting nitrogen into the vacuum box 3 from the vacuum valve 802, thus forming a protected environment; and then open the blind flange at the position where the electron transmitting unit is connected and installing the electron transmitting unit one by one; after all of the electron transmitting units are installed, sucking by the vacuum valve 802 connected to the external vacuum sucking system and baking and venting again to make high vacuum inside the vacuum box 3; the cathode of each electron transmitting unit can be activated during baking and venting; after the baking and venting is finished, closing the vacuum valve 802 to maintain high vacuum in the vacuum 3; during the operating of the grid-controlled distributed x-ray apparatus, the small amount of gas generated by the anode is withdrawn out by the vacuum pump 801 so as to maintain high vacuum inside the vacuum box 3. When an electron transmitting unit damages or needs replacement due to the expiry of its service time, nitrogen is injected into the vacuum box 3 from the vacuum valve 802 to establish protection; removing the electron transmitting unit to be replaced and install a new one with the least time; vacuum valve 802 connected to the external vacuum sucking device to draws vacuum to vacuum box 3; when high vacuum is achieved once again in the vacuum box 3, close the vacuum valve 802 to maintain high vacuum inside the vacuum box 3.

Figure 10:
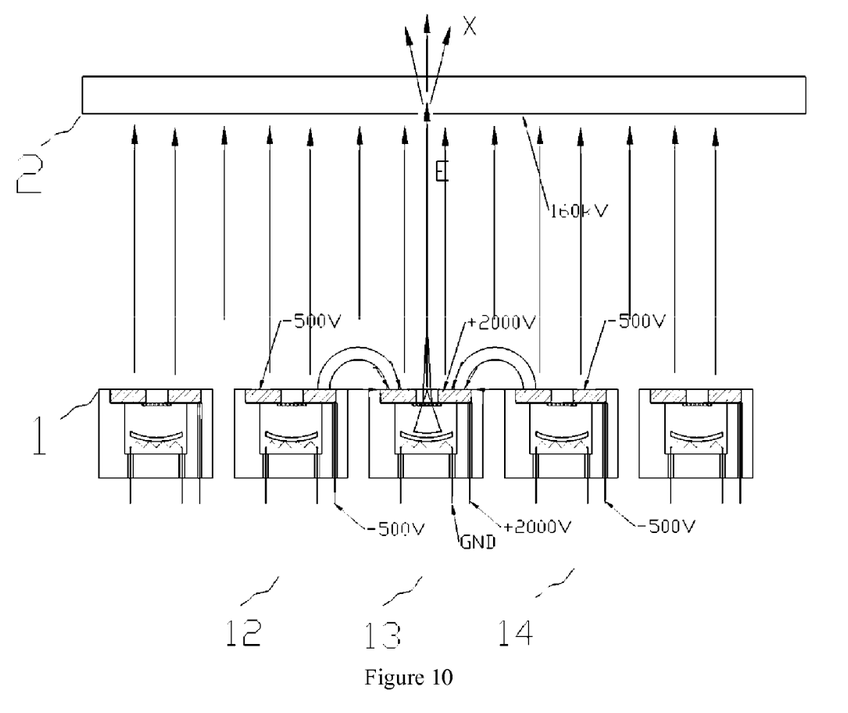
FIG. 10 depicts a schematic view of automatic focus conducted by employing the grid control of the present application.

It should be noted that if the grid-controlled apparatus 703 only change the state of the grid of one of the adjacent electron transmitting units, at the same time only one of the adjacent electron transmitting units transmits electron forming the electron beam current, the electric field on both sides of the grid of the electron transmitting unit automatically focuses the electron beam current. As shown in FIG. 10, the arrow between the electron transmitting unit 1 and the anode 2 indicates the direction that the electrons move toward (against the direction of power line). In FIG. 10, the voltage of anode 2 is high voltage of +160 kV and the arrow between the electron transmitting unit 1 and the anode 2 in the large electric field directs to the anode 2 from the electron transmitting unit 1. That is to say, as long as the electron transmitting unit 1 transmits the electron beam current, the electron beam current will move toward anode 2. Observing the state of partial electrical field of the surface of the electron transmitting unit 1, in the adjacent electron transmitting units 12, 13 and 14, the voltage of the grid 103 of the electron transmitting unit 13 changes from −500V to +2000V, then electron transmitting unit 13 enters into the electron transmitting state and the voltage of the grid 103 of the adjacent electron transmitting units 12 and 14 remains −500V. If electrons are transmitted by the electron transmitting units 12, 14, the electrons move toward the grid 103 of electron transmitting unit 13 from the grids of the electron transmitting units 12 and 14. However, because electrons are not transmitted by the electron transmitting units 12, 14, the electron beam transmitted by the electron transmitting unit 13 is squeezed by the effect of electric field directing to the adjacent electron transmitting units 12 and 14 from the electron transmitting unit 13, and hence having the automatic focusing effect.

Figure 11:
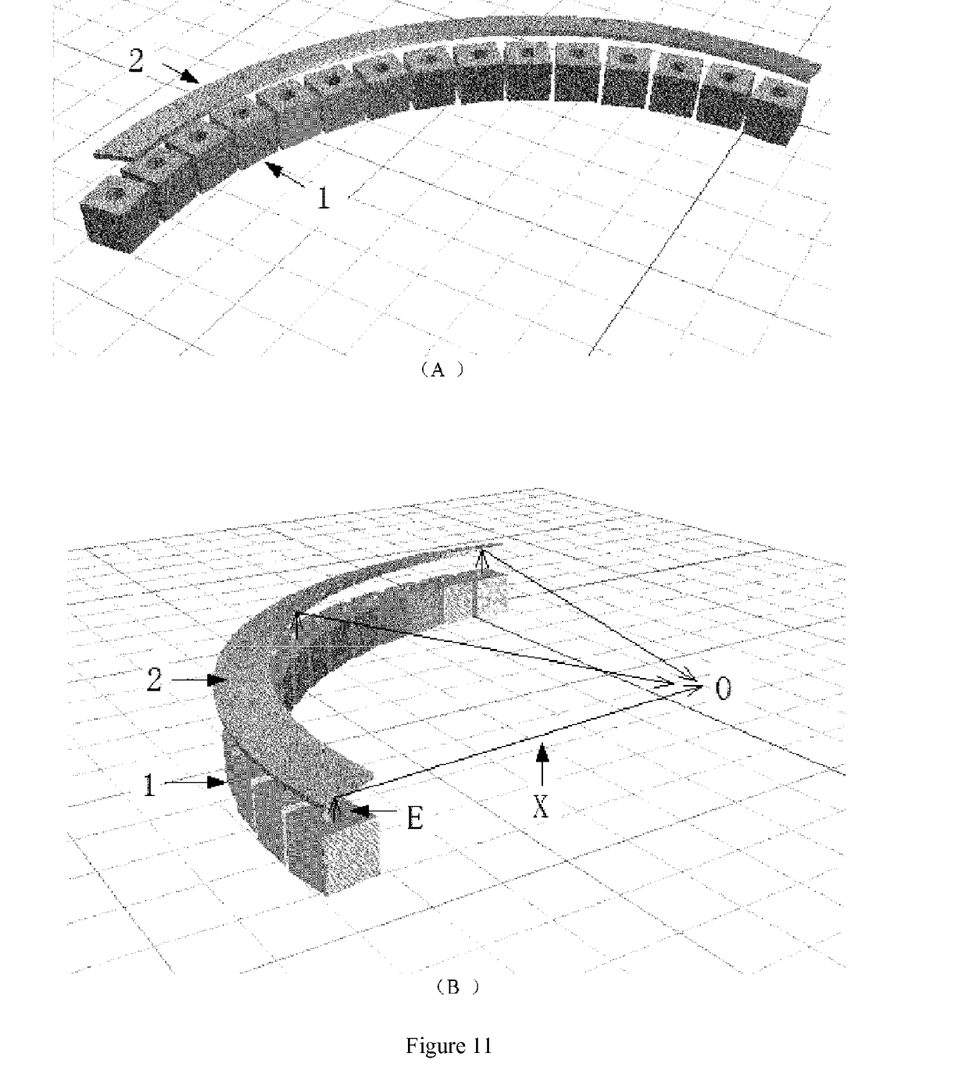
FIG. 11 depicts a schematic view of the configuration of electron transmitting unit and the anode inside the arc-shaped grid-controlled distributed x-ray apparatus of the present application, wherein (A) is the view observed from the center of the arc and (B) is the view observed from one end of the arc.

What's more, it should be noted that the grid-controlled distributed x-ray apparatus of this disclosure can be in linear arrangement or cambered arrangement so as to meet different application requirements. FIG. 11 shows a schematic view of the configuration of electron transmitting unit and the anode inside the vacuum box of the arc grid-controlled distributed x-ray apparatus of the present application, wherein (A) is the view observed from the center of the arc and (B) is the view observed from one end of the arc. It should be noted that the electron transmitting unit 1 in FIG. 11 only reflects those portions inside the vacuum box 3 and the shape of the electron transmitting unit 1 is rectangular. The electron transmitting unit 1 is arranged along the circumference in a plane and the size of arc arranged can be set as needed. The anode 2 is disposed above the electron transmitting unit 1 being a circular arc conical surface with the inner high and the outer low. That is, in the direction of arc, it is parallel to the arc that the electron transmitting unit 1 is in. There is a small angel between the axial direction of the arc and the upper surface of the electron transmitting unit 1, similar to the structure of a compass roof. The electron beam current is transmitted from the upper surface of the electron transmitting unit 1 and accelerated by the high voltage electric field between the anode 2 and the electron transmitting unit 1, and finally bombards the anode 2 forming a series of x-ray target spots in arc shape on the anode 2. Useful transmitting direction of x-ray directs to the center O of the arc. With regards to the vacuum box 3 of the arc grid-controlled distributed x-ray apparatus is arc-shaped or termed as ring-shaped corresponding to the configuration of the electron transmitting unit 1 and the shape of anode 2 inside it. The x-rays transmitted by the arc distributed x-ray apparatus are directed to the center O of the arc and are able to be applied to the case that needs the source of ray to be in a circular arrangement.

In addition, it should be noted that in the grid-controlled distributed x-ray apparatus, the grid and the electron transmitting unit can be separated.

In addition, it should be noted that in the grid-controlled distributed x-ray apparatus, the arrangement of each electron transmitting unit may be linear or segmented linear, such as L-shaped or U-shaped. What's more, the arrangement of each electron transmitting unit may be arc or segmented arc, e.g. curve connected by curved segments of different diameters or the combination of linear segments with curved segments etc.

In addition, it should be noted that in the grid-controlled distributed x-ray apparatus, the arrangement space between each electron transmitting unit may be uniform or nonuniform.

Embodiments
(System Configuration)

As shown in FIG. 1-9, the grid-controlled distributed x-ray apparatus of this disclosure includes a plurality of electron transmitting unit 1, an anode 2, a vacuum box 3, a high voltage power supply connecting means 4, a filament power supply connecting means 5, a connecting means of grid-controlled apparatus 6, a vacuum means 8 and a power supply and control system 7. The plurality of electron transmitting units 1 are installed on the wall at the lower end of the vacuum box 3 in a liner arrangement. The cathode end of the electron transmitting unit 1 is located inside the vacuum box and the lead end of the electron transmitting unit 1 is located outside of the vacuum box 3. Each electron transmitting unit 1 is independent to each other. The anode 2 in a shape of strip is installed at the upper end inside the vacuum box 3. In the direction of linear arrangement, anode 2 is parallel to the electron transmitting unit 1. In the vertical cross section of the linear arrangement, there is a small angle between the anode 2 and the upper surface of the electron transmitting unit 1. The high voltage power supply connecting means 4 is installed at the upper end of the vacuum box 3, the interior thereof is connected to the anode 2 and the exterior thereof is pluggable to the high voltage cable. The filament lead 105 of each electron transmitting unit 1 is connected to the filament power supply 704 by the filament power supply connecting means 5. The grid lead 108 of each electron transmitting unit 1 is connected to the grid-controlled apparatus 703 by the connecting means of grid-controlled apparatus 6. The vacuum means 8 including a vacuum pump 801 and a vacuum valve 802 is installed on the side wall of the vacuum box 3. The power supply and control system 7 includes multiple modules including a control system 701, a high voltage power supply 702, a grid-controlled apparatus 703, a filament power supply 704, a vacuum power supply 705 etc., those of which are connected to the components of the system including the heating filaments 101 of multiple electron transmitting units 1, grid 103 and anode 2, vacuum means 8 etc by power cable and controlling cable.

(Operating Principle)

In the grid-controlled distributed x-ray apparatus of this disclosure, the power supply and control system 7 controls the filament power supply 704, the grid-controlled apparatus 703 and the high voltage power supply 702. Under the effect of the filament power supply 704, the cathode 102 is heat to high temperature (e.g. 500-2000° C.) transmitting state by the heating filament 101 and a large number of electrons are generated at the surface of the cathode 102. Each grid 103 is in the negative voltage, e.g. −500V, due to the grid-controlled apparatus 703. A negative electric field is formed between the grid 103 of each electron transmitting unit 1 and the cathode 102 and the electrons are limited to the surface of the cathode 102. Anode 2 is in a much high positive voltage, e.g. positive dozens of KV to hundreds of KV, due to the high voltage 702, and a positive accelerating electric field is formed between the electron transmitting unit 1 and the anode 2. In the case that needs generating x-ray, the output of a certain path of the grid-controlled apparatus 703 is converted from negative voltage to positive voltage by the power supply and control system 7 following instruction or preset program. The output signal of each path is converted in accordance with the time sequence, for example, the voltage of the output channel 1 of the grid-controlled apparatus 703 is changed from −500V to +2000V at the moment 1. In the corresponding electron transmitting unit 11, the electric field between the grid 103 and the cathode 102 is changed to positive. The electrons move to the grid 103 from the surface of the cathode 102 and enter into the positive electric field between the electron transmitting unit 11 and anode 2 through the grid mesh 107. Thus, the electrons are accelerated and changed to high energy, and finally bombard the anode 2 forming a target spot 21 on the anode 2. Moreover, x-rays are transmitted at the position of target spot 21. The voltage of the output channel 2 of the grid-controlled apparatus 703 is changed from −500V to +2000V at the moment 2. The corresponding electron transmitting unit 12 transmits electrons, thus forming a target spot 22 on the anode 22 and the x-rays are transmitted at the target spot 22. The voltage of the output channel 3 of the grid-controlled apparatus 703 is changed from −500V to +2000V at the moment 3. The corresponding electron transmitting unit 13 transmits electrons, thus forming a target spot 23 on the anode 22 and the x-rays are transmitted at the target spot 23. The rest can be done in the same manner. Then x-rays are transmitted at the target spot 24, and than x-rays are transmitted at the target spot 25 and that cycle repeats. Therefore, the power supply and control system 7 makes each electron transmitting unit 1 work alternately to transmit electron beam following a predetermined time sequence and generate x-rays alternately at different positions of anode 2 so as to become the distributed x-ray source.

In addition, the gas generated when the anode 2 is bombarded by the electron beam current is drawn out by the vacuum pump 801 in real time, and a high vacuum is maintained in the vacuum box 3, thus facilitating the stable operation for a long time. In addition to control each power supply to drive each component working coordinately following the preset program, the power supply and control system 7 also can receive external command by the communication interface and the human-computer interface and modify and set key parameters of the system as well as update the program the adjust automatic control.

In addition, the grid-controlled distributed x-ray light source of this disclosure can be applied to CT device so as to obtain a CT device of good stability, excellent reliability and high efficiency for inspection.

(Effects)

The disclosure provides a grid-controlled distributed x-ray apparatus generating x-rays changing the focus position periodically in a predetermined sequence in a light source device. By employing the thermionic cathode, the electron transmitting unit of this disclosure has the advantages of larger transmitting current, longer service life and more matured technology compared with other current design. It is easy to assemble, flexible to control and convenient to maintain because multiple electron transmitting units are fixed to the vacuum box respectively. The state conversion can be prompt and concise and it is ready to make out multiple operating states by controlling the operating state of each electron transmitting unit via the control of the grid. The overheat of the anode is remitted by employing the design of big anode in the shape of strip thus improving the power of the light source. The electron transmitting units can be in a linear arrangement rendering the overall to be a linear distributed x-ray apparatus or an annular arrangement rendering the overall to be an annular distributed x-ray apparatus, so as to meet various service conditions and have flexible applications. By the design to control the voltage via grid, an automatic focusing effect of the electron beam generated by each electron transmitting unit can be obtained and small target spot could be achieved. Compared with other distributed x-ray light source device, the one in this disclosure has the advantages of large current, small target spot, uniform target spots and high repeatability, high output power, simple structure, convenient control and low cost.

In addition, applying the grid-controlled distributed x-ray light source to the CT device, multiple visual angles can be generated without moving the light source, and therefore the movement of slip ring could be omitted. This contributes to simplify the structure, enhance the stability and reliability of the system, hence increasing the efficiency of inspection.

Embodiments have been disclosed above for the purpose of illustration but are not limited thereto. It should be appreciated that various modifications and combination are possible without departing from the scope and spirit of the accompanying claims.

LIST OF REFERENCE NUMBERS

1: electron transmitting unit
2: anode;
3: vacuum box;
4: high voltage power supply connecting means;
5: filament power supply connecting means;
6: connecting means of grid-controlled apparatus;
7: power supply and control system;
8: vacuum means;
E: electronic beam current;
X: x-ray;
101: heating filament;
102: cathode;
103: grid;
104: insulated support;
105: filament lead;
106: grid frame;
107: grid mesh;
108: grid lead;
109: connecting fastener;
701: control system;
702: high voltage power supply;
703: grid-controlled apparatus;
70301: controller;
70302: negative high voltage module;
70303: positive high voltage module;
704: filament power supply;
801: vacuum pump;
802: vacuum valve;

The invention claimed is:
1. An x-ray apparatus comprising:
a single vacuum box sealed at a periphery thereof and having an interior maintained at high vacuum;
a plurality of electron transmitting units arranged in a linear array and installed on a wall at one end within the vacuum box, each electron transmitting unit being independent of one another and comprising:

a heating filament,
a cathode connected to the heating filament, and
a grid arranged above the cathode and opposing the cathode;
wherein the linear array contains a plurality of cathodes that are spaced apart from one another with a single grid arranged above each cathode; and
a single anode made of metal and installed at an opposing end of the vacuum box with respect to the plurality of electron transmitting units, the anode being strip shaped;
wherein in a direction of length, the anode is parallel to a plane of the grid of each electron transmitting unit, and in a direction of width, the anode has a predetermined angle with respect to the plane of the grid of each electron transmitting unit.

2. The x-ray apparatus according to claim 1, further comprising:
a power supply and control system having a high voltage power supply connected to the anode;
a filament power supply connected to each electron transmitting unit;
a grid-controlled apparatus connected to each electron transmitting unit; and
a control system configured to control each power supply.

3. The x-ray apparatus according to claim 2, wherein each electron transmitting unit comprises:
a filament lead extending from opposing ends of the heating filament and connected to the filament power supply;
an insulated support having an opening and enclosing the heating filament and the cathode; and
a connecting fastener connected at a lower end of the insulated support.

4. The x-ray apparatus according to claim 3, wherein the grid comprises:
a grid frame which is made of metal and contains an opening in the center;
a grid mesh which is made of metal and fixed at the opening of the grid frame; and
a grid lead extending from the grid frame and connected to the grid-controlled apparatus;
wherein the grid is configured on the opening of the insulated support, the filament lead and the grid lead pass through the insulated support and extend outside the electron transmitting unit, and the connecting fastener is seal connected to the wall of the vacuum box.

5. The x-ray apparatus according to claim 4, wherein the insulated support is a cylinder, and the grid frame, the cathode and the grid mesh are circular.

6. The x-ray apparatus according to claim 4, wherein the insulated support is a cylinder, and the grid frame, the cathode and the grid mesh are rectangular.

7. The x-ray apparatus according to claim 4, wherein the insulated support is cuboid, and the grid frame, the cathode and the grid mesh are circular.

8. The x-ray apparatus according to claim 4, wherein the insulated support is cuboid, and the grid frame, the cathode and the grid mesh are rectangular.

9. The x-ray apparatus according to claim 4, wherein the grid mesh is flat, spherical or U-shaped groove.

10. The x-ray apparatus according to claim 2, further comprising:
a high voltage power supply connecting means for connecting the anode to the high voltage power supply and installed on a side wall of the vacuum box adjacent to the anode;
a filament power supply connecting means for connecting the heating filament to the filament power supply; and
a connecting means of the grid-controlled apparatus for connecting the grid of each electron transmitting unit to the grid-controlled apparatus.

11. The x-ray apparatus according to claim 2, further comprising:
a vacuum power supply included in the power supply and control system; and
a vacuum means installed on a side wall of the vacuum box for maintaining the high vacuum in the vacuum box by using the vacuum power supply.

12. The x-ray apparatus according to claim 2, wherein the grid-controlled apparatus comprises:
a controller;
a negative high voltage module;
a positive high voltage module; and
a plurality of high voltage switch elements, each of the plurality of high voltage switch elements at least comprising a control end, two input ends, and an output end, and a withstand voltage between the control end and the output end each being larger than a maximum voltage formed by the negative high voltage module and the positive high voltage module;
wherein the negative high voltage module is configured to provide a stable negative high voltage to one input end of each of the plurality of high voltage switch elements, the positive high voltage module is configured to provide a stable positive high voltage to the other input end of each of the plurality of high voltage switch elements, the controller is configured to control independently each of the plurality of high voltage switch elements, the grid-controlled apparatus further comprises a plurality of control signal output channels, and one output end of each high voltage switch element is connected to one of the control signal output channels.

13. The x-ray apparatus according to claim 1, wherein the vacuum box is made of glass or ceramic.

14. The x-ray apparatus according to claim 1, wherein the vacuum box is made of metal.

15. The x-ray apparatus according to claim 1, wherein the plurality of electron transmitting units are disposed in a linear or segmented linear fashion.

16. The x-ray apparatus according to claim 1, wherein a spacing between each electron transmitting unit is uniform.

17. The x-ray apparatus according to claim 1, wherein a spacing between each electron transmitting unit is non-uniform.

18. A CT device comprising: the x-ray apparatus according to claim 1.

* * * * *